United States Patent [19]

Agback

[11] Patent Number: 4,628,083

[45] Date of Patent: Dec. 9, 1986

[54] 2-HYDROXY-5-(ARYLAZO)-BENZENE ALKANOIC ACIDS

[75] Inventor: Karl H. Agback, Upsala, Sweden

[73] Assignee: Pharmacia AB, Uppsala, Sweden

[21] Appl. No.: 692,417

[22] Filed: Jan. 18, 1985

Related U.S. Application Data

[63] Continuation of Ser. No. 542,508, Oct. 17, 1983, abandoned.

[51] Int. Cl.$^4$ .................. A61K 31/655; C07C 107/06; C09B 29/14; C09B 43/136
[52] U.S. Cl. .................................... 534/798; 534/590; 534/592; 534/774; 534/851; 534/853; 534/887
[58] Field of Search ............... 260/152, 157, 207, 154, 260/156; 534/853, 774, 787, 798, 851

[56] References Cited

U.S. PATENT DOCUMENTS

| | | | |
|---|---|---|---|
| 2,396,145 | 3/1946 | Anders et al. | 260/156 |
| 3,214,436 | 10/1965 | Boyle et al. | 260/207 |
| 3,249,599 | 5/1966 | May et al. | 260/196 |
| 3,370,910 | 2/1968 | Crotte et al. | 260/207 X |
| 3,681,319 | 8/1972 | Lindberg | 260/156 |
| 3,915,951 | 10/1975 | Agback et al. | 260/156 |
| 4,045,429 | 8/1977 | Agback | 260/207 |
| 4,153,599 | 5/1979 | Rosati | 260/207 |

OTHER PUBLICATIONS

Kornfeld et al, J. Amer. Chem. Soc., vol. 70, pp. 1373 to 1376 (1948).

*Primary Examiner*—Floyd D. Higel
*Attorney, Agent, or Firm*—Fred Philpitt

[57] ABSTRACT

The invention relates to new arylazo compounds of the general formula

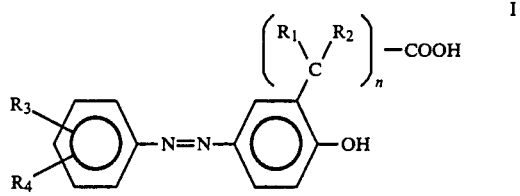

wherein $R_1$ and $R_2$ independently of each other represent hydrogen or $C_{1-3}$ alkyl, $R_3$ represents hydrogen, halogen, $C_{1-3}$ alkyl, $C_{1-3}$ alkoxy, carboxy, $C_{1-3}$ alkoxycarbonyl, $C_{1-3}$ alkylcarbonyl or a group X—NH—SO$_2$—, wherein X represents a heterocyclic ring, $R_4$ represents hydrogen, halogen or $C_{1-3}$ alkyl, and n is the integer 1 or 2, the two groups

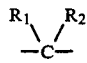

being the same or different when n is 2, and lactones and salts thereof. The compounds of formula I have a high inhibiting effect on prostaglandin synthetizing and inactivating enzymes and may therefore be used as a drug and anti-fertility agent. The invention also relates to preparation of the compounds of formula I as well as pharmaceutical compositions containing the same.

6 Claims, No Drawings

2-HYDROXY-5-(ARYLAZO)-BENZENE ALKANOIC ACIDS

This is a continuation of application Ser. No. 542,508 filed Oct. 17, 1983 abandoned and the benefits of 35 USC 120 are claimed relative to it.

The present invention relates to new arylazo compounds, pharmaceutical preparations containing these compounds and processes for the preparation of the compounds.

The new arylazo compounds have a surprisingly strong inhibiting effect on enzymes, which synthetize and inactivate prostaglandins, whereby they can influence and modify the effect of the prostaglandins.

The new compounds according to the invention are represented by the general formula

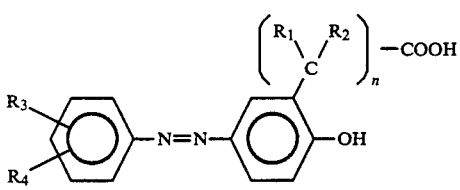

wherein $R_1$ and $R_2$ independently of each other represent hydrogen or $C_{1-3}$ alkyl, $R_3$ represents hydrogen, halogen, $C_{1-3}$ alkyl, $C_{1-3}$ alkoxy, carboxy, $C_{1-3}$ alkylcarbonyl, $C_{1-3}$ alkoxycarbonyl or a group X—NH—SO$_2$—, wherein X represents a heterocyclic ring, $R_4$ represents hydrogen, halogen or $C_{1-3}$ alkyl, and n is the integer 1 or 2, the two groups

being the same or different when n=2, and lactones as well as pharmacologically acceptable salts thereof.

When the radicals $R_1$–$R_4$ represent or contain $C_{1-3}$ alkyl or $C_{1-3}$ alkoxy the latter groups are preferably methyl or ethyl, and methoxy or ethoxy respectively, particularly methyl and methoxy. The symbol X preferably represents a monocyclic, suitably unsaturated heterocyclic ring, which preferably has 5–6 ring members. The heterocyclic ring preferably contains one or two hetero atoms, selected from nitrogen, oxygen and sulfur. As examples of such heterocyclic ring systems pyridyl, pyrimidyl, pyrazinyl, oxazole, thiazole, and the like may be mentioned. The heterocyclic ring X may optionally be substituted by one or more substituents selected from halogen and low-alkyl (having 1–6 carbon atoms, particularly 1–3 carbon atoms). Examples of suitable pharmacologically acceptable salts are alkali metal, alkaline-earth metal and (optionally substituted) ammonium salts.

As examples of suitable compounds according to the invention the following compounds may be mentioned:
2-hydroxy-5[4-[[(2-pyridinyl)-amino]sulfonyl]-phenylazo]benzeneacetic acid,
2-hydroxy-5-[4-[[(2-pyridinyl)-amino]-sulfonyl]-phenylazo]benzenepropanoic acid,
2-hydroxy-5-[4-[[(3,4-dimethyl-5-isoxazolyl)amino]sulfonyl]phenylazo]benzeneacetic acid,
2-hydroxy-5-[4-[[(4,5-dimethyl-2-oxazolyl)amino]sulfonyl]phenylazo]benzenepropanoic acid,
2-hydroxy-5-[4-[[(4,6-dimethyl-2-pyrimidinyl)-amino]-sulfonyl]phenylazo]benzenepropanoic acid,
2-hydroxy-5-[4-[[(4,6-dimethyl-2-pyrimidinyl)-amino]-sulfonyl]phenylazo]benzeneacetic acid,
2-hydroxy-5-[4-[[(2-pyridinyl)amino]-sulfonyl]-phenylazo]-α,α-dimethylbenzeneacetic acid,
2-hydroxy-5-phenylazo-benzeneacetic acid,
2-hydroxy-5-phenylazo-benzenepropanoic acid,
2-hydroxy-5-(4-methoxy-phenylazo)benzeneacetic acid,
5-(4-chloro-phenylazo)-2-hydroxy-benzeneacetic acid,
5-(3-chloro-phenylazo)-2-hydroxy-benzeneacetic acid,
5-(2-chloro-phenylazo)-2-hydroxy-benzenepropanoic acid,
2-hydroxy-5-(4-methyl-phenylazo)benzenepropanoic acid,
5-(4-ethoxycarbonyl-phenylazo)-2-hydroxy-benzeneacetic acid,
5-(3-chloro-4-methyl-phenylazo)-2-hydroxy-benzeneacetic acid,
5-(3-chloro-4-methyl-phenylazo)-2-hydroxy-benzenepropanoic acid,
5-(4-carboxy-phenylazo)-2-hydroxy-benzeneacetic acid,
4-[(2-oxo-5(2H)-benzofuranyl)-azo]-N-(2-pyridinyl)-benzenesulfonamide,
4-[(3,4-dihydro-2-oxo-2H-1-benzopyran-6-yl)-azo]-N-(2-pyridinyl)benzenesulfonamide.

The compounds of formula I according to the invention can be prepared by several different methods known per se, e.g. according to one of the following methods:

1. Diazotization of a compound of the general formula II

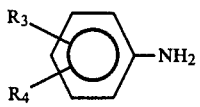

wherein $R_3$ and $R_4$ are as defined above,
and coupling in an alkaline medium with a compound of the general formula III

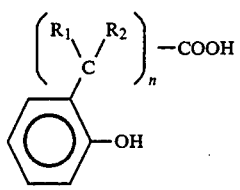

wherein $R_1$, $R_2$ and n are as defined above.

2. Reaction of a sulfonyl chloride of the formula

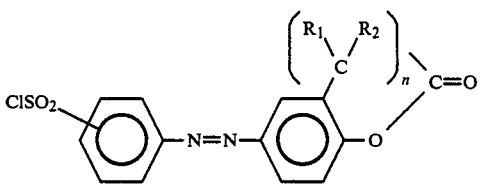

wherein $R_1$, $R_2$ and n are as defined above,
with an amine of the formula $$X-NH_2 \quad \quad V$$

wherein X is as defined above,
in the presence of a basic condensation agent.

The starting material of method (2) may e.g. be obtained from sulfanilic acid, which is diazotized and coupled with a compound of the formula III analogously with the described method (1), whereupon the azo compound formed through treatment with a dehydrating agent is converted into a lactone of the general formula

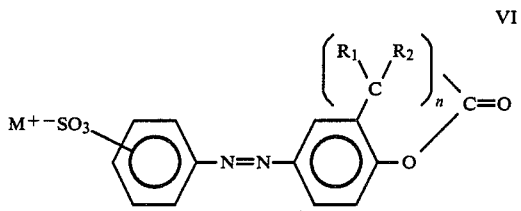

wherein $R_1$, $R_2$ and n are as defined above and $M^+$ is an alkali metal cation. The starting material of formula IV is then obtained in known manner through chlorination of the sulfonate VI.

The compounds of formula I are easily converted into the corresponding lactones and vice versa. For example, the open-ring acid of formula I is converted into the corresponding lactone by heating, particularly in acidic medium. The compounds are generally soluble in organic solvents in their lactone form, while in buffered neutral or basic aqueous systems they exist as soluble salts of the open-ring form.

As mentioned above the new compounds of formula I, as well as the corresponding lactones and salts, are characterized by a surprisingly high inhibiting effect on prostaglandin synthetizing and inactivating enzymes, which has been verified in i.a. experiments relating to the effect on the prostaglandin metabolism of human placenta. They may therefore be used i.a. in treatment of inflammatory diseases, such as rheumatoid arthritis and ulcerative colitis, as male anti-fertility agents, etc. The inhibiting effect of the compounds on the inactivation of prostaglandins has been shown by experiments in vitro as follows:

Radioactive prostaglandin $F_{2\alpha}$ was incubated with cellfree preparations of different organs (containing prostaglandin-15-dehydrogenase) according to Hoult and Moore, British Journal of Pharmacology, Vol. 61 (1977), p. 615. After a suitable time the prostaglandins were extracted and separated by chromatography. Then the amount of remaining prostaglandin $F_{2\alpha}$ was compared with the amounts of metabolites. The inhibiting effect was obtained by the addition of the compounds according to the invention during the incubation and comparison with control experiments without such addition. The results may be represented either as a concentration giving 50% inhibition of the prostaglandin inactivation, or as an inhibition in percent at a certain concentration of the studied compound. In the following table the results for some compounds according to the invention are shown compared to the known drug sulfasalazine.

In the table, compound
A is sulfasalazine,
B is 2-hydroxy-5-[4-[[(2-pyridinyl)amino]sulfonyl]-phenylazo]benzeneacetic acid,
C is 2-hydroxy-5-phenylazo-benzeneacetic acid.

TABLE

| Organ | Compound | Concentration μM | (μg/ml) | Inhibition, % |
|---|---|---|---|---|
| Human placenta | A | 95 | (38) | 50 |
| Human placenta | B | 1,9 | (0,78) | 50 |
| Human placenta | B | 50 | (20,6) | 87,5 |
| Rat stomach | B | 2 | (0,82) | 67,2 |
| Rat colon | B | 2 | (0,82) | 53,3 |
| Rat colon | A | 50 | (19,9) | 47,8 |
| Rat colon | C | 50 | (12,8) | 71,3 |
| Rat kidney | B | 2 | (0,82) | 94,1 |
| Rat lung | B | 2 | (0,82) | 85,2 |
| Guinea pig duodenum | B | 2 | (0,82) | 68,3 |
| Guniea pig colon | B | 2 | (0,82) | 58,7 |
| Guniea pig kidney | B | 2 | (0,82) | 53,8 |
| Guinea pig kidney | B | 50 | (20,6) | 65,9 |
| Guinea pig kidney | C | 50 | (12,8) | 45,4 |

As the inhibition expressed as percent is linear against the logarithm of the concentration, even rather small differences in percent inhibition are important. The table shows that compound B according to the invention is 50 times as active as the known compound A, which has been the hitherto most active one of earlier known compounds. Even the structurally most simple compound according to the invention, C, is significantly more active than compound A.

The invention also comprises pharmaceutical preparations containing the compounds of the invention in combination with an organic or inorganic inert carrier material suitable for oral, rectal or parenteral application. The pharmaceutical preparations may exist in solid, semi-solid or liquid form, and they may optionally be sterilized and/or contain additional adjuvants. The pharmaceutical preparations may be prepared in a manner well known to every person skilled in the art by mixing the active substance with the carrier material and possible additional adjuvants and converting the mixture obtained into a suitable galenic form. As a dosage guide line a daily dosis of 5–5,000 mg per day may be indicated.

The invention will be illustrated further in the following specific examples, which, however, in no way are intended to restrict the scope of the invention.

EXAMPLE 1

2-hydroxy-5-[4-[[(2-pyridinyl)-amino]sulfonyl]-phenylazo]benzene-acetic acid 12 g sulfapyridine was dissolved with cooling to 0° C. in 40 ml water and 12 ml conc. hydrochloric acid. 3.5 g sodium nitrite in 20 ml water was added to the sulfapyridine solution during about 15 minutes with stirring and cooling. The diazonium salt solution was added to 7.6 g 2-hydroxy-benzeneacetic acid and 7 g sodium hydroxide in 50 ml water at 0°–10° C. After stirring for 1.5 h the solution was acidified by hydrochloric acid. The precipitating product was filtered off and washed with water. Yield 18.1 g. The product was dissolved in acetic acid and treated with 5 g decolourizing coal. The solution was filtered and evaporated in vacuum. This was repeated once, a pure product being obtained, which during partial melting at about 135° C. was converted into another crystal modification of melting point 185°–187° C. with decomposition.

EXAMPLE 2

4-[(2-oxo-5(2H)-benzofuranyl)-azo]-N-(2-pyridinyl)-benzenesulfonamide 4.0 g of the acid produced according to Example 1 was heated with 65 ml acetic acid, 2 ml acetic anhydride and 0.25 ml conc. sulfuric acid until a clear solution was obtained. 25 ml water was added and the solution was cooled to room temperature, the product crystallizing. After filtration and washing with water 2.1 g of the title compound was obtained, which melted at 231° C. with decomposition.

EXAMPLE 3

2-hydroxy-5-[4-[[(2-pyridinyl)-amino]-sulfonyl]-phenylazo]benzenepropanoic acid 25.0 g of sulfapyridine was dissolved in 80 ml of water and 24 ml of conc. hydrochloric acid. The solution was kept at 0° C. 7.0 g of sodium nitrite in 40 ml of cold water was added during about 10 min. with stirring and cooling by the addition of 100 g ice in portions.

14.8 g of 3,4-dihydro-(2H)-1-benzopyran-2-one (the lactone of 2-hydroxy-benzene-propanoic acid) was added to 16 g of sodium hydroxide in 200 ml of water. The mixture was heated to 80°-90° C. until all of the lactone had been hydrolyzed and dissolved. The solution was cooled to about 0° C. and the diazonium salt solution quickly added with stirring. After 5 min., the solution was acidified with dilute hydrochloric acid. An oily mass precipitated. After decantation of the aqueous phase and digestion with 200 ml of acetone, the product crystallized and was filtered off. It was dissolved in 500 ml of water and 5 g of sodium hydroxide and carefully precipitated by the addition of acetic acid. The yield was 24.3 g. Melting point 188°-190° C.

EXAMPLE 4

By the application of the procedures given in Example 1 and 3 the following compounds were obtained after purification by recrystallization from acetic acid, alcohol or ethylene-dichloride or by reprecipitation from an alkaline water solution by the addition of a mineral acid, formic or acetic acid:

(a) 2-Hydroxy-5-[-4-[[(4,5-dimethyl-2-oxazolyl)amino]-sulfonyl]phenylazo]benzenepropanoic acid. Melting point: 206° C. with decomposition.

(b) 2-Hydroxy-5-[4-[[(4,6-dimethyl-2-pyrimidinyl)-amino]sulfonyl]phenylazo]benzeneacetic acid. Melting point: 180° C. with decomposition.

(c) 2-Hydroxy-5-phenylazo-benzeneacetic acid. Melting point: 165°-167° C.

(d) 2-Hydroxy-5-phenylazo-benzenepropanoic acid. Melting point: 147°-148° C.

(e) 2-Hydroxy-5-(4-methoxy-phenylazo)benzeneacetic acid. Melting point: 211° C. with decomposition.

(f) 5-(4-Chloro-phenylazo)-2-hydroxy-benzeneacetic acid. Melting point: 193°-195° C.

(g) 5-(3-Chloro-phenylazo)-2-hydroxy-benzeneacetic acid. Melting point: 166°-168° C.

(h) 5-(2-Chloro-phenylazo)-2-hydroxy-benzenepropanoic acid. Melting point: 149°-151° C.

(i) 2-Hydroxy-5-(4-methyl-phenylazo)benzenepropanoic acid. Melting point: 139°-141° C.

(j) 5-(4-Ethoxycarbonyl-phenylazo)-2-hydroxy-benzeneacetic acid. Melting point: 214°-216° C.

(k) 5-(3-Chloro-4-methyl-phenylazo)-2-hydroxy-benzenepropanoic acid. Melting point: 127°-129° C.

(l) 5-(4-Carboxy-phenylazo)-2-hydroxy-benzeneacetic acid. Melting point: 254° C. with decomposition.

What I claim is:

1. An arylazo compound of the general formula

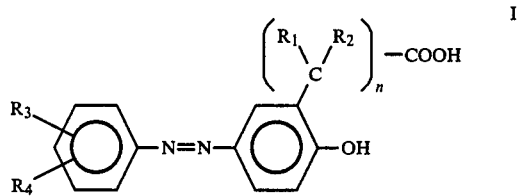

wherein $R_1$ and $R_2$ independently of each other represent hydrogen or $C_{1-3}$ alkyl, $R_3$ represents hydrogen, halogen, $C_{1-3}$ alkyl, $C_{1-3}$ alkoxy, carboxy, $C_{1-3}$ alkoxycarbonyl, $C_{1-3}$ akylcarbonyl or a group X—NH—$SO_2$—, wherein X represents a heterocyclic ring, $R_4$ represents hydrogen, halogen or $C_{1-3}$ alkyl, and n is the integer 1 or 2, the two groups

being the same or different when n is 2, or a lactone or a salt thereof.

2. An arylazo compound according to claim 1, wherein X is a monocyclic, unsaturated heterocyclic ring, which optionally is substituted or by one or more low-alkyl groups or halogen atoms.

3. An arylazo compound according to claim 1, wherein $R_1$ and $R_2$ are hydrogen.

4. An arylazo compound according to claim 1, wherein $R_3$ represents hydrogen, halogen, methyl, carboxy, methoxycarbonyl, ethoxycarbonyl, methoxy or X—NH—$SO_2$, wherein X represents a heterocyclic ring, and $R_4$ represents hydrogen.

5. An arylazo compound according to claim 1, wherein n=1.

6. The arylazo compound according to claim 1, 2-hydroxy-5-[4[[(2-pyridinyl)-amino]sulfonyl]phenylazo]-benzeneacetic acid.

* * * * *